United States Patent [19]

Cotteret

[11] Patent Number: 5,500,022
[45] Date of Patent: Mar. 19, 1996

[54] PROCESS FOR DYEING KERATINOUS FIBRES WITH 2,6-DIMETHYL-1,4-DIAMINOBENZENE AND/OR 2,3-DIMETHYL-1,4-DIAMINOBENZENE AND/OR 2,6-DIETHYL-1,4-DIAMINOBENZENE IN AN ACID MEDIUM AND COMPOSITIONS EMPLOYED

[75] Inventor: Jean Cotteret, Verneuil-sur-Seine, France

[73] Assignee: L'Oreal, Paris, France

[21] Appl. No.: 421,739

[22] Filed: Apr. 13, 1995

Related U.S. Application Data

[63] Continuation of Ser. No. 274,711, Jul. 18, 1994, abandoned, which is a continuation of Ser. No. 996,193, Dec. 23, 1992, abandoned, which is a continuation of Ser. No. 708,380, May 31, 1991, abandoned.

[30] Foreign Application Priority Data

May 31, 1990 [FR] France .................................. 90 06802

[51] Int. Cl.$^6$ ........................................................ A61K 7/13
[52] U.S. Cl. .......................... 8/410; 8/406; 8/408; 8/411; 8/412; 8/416
[58] Field of Search ................................ 8/405, 406, 408, 8/409, 410, 411, 412, 416, 429

Primary Examiner—Paul Lieberman
Assistant Examiner—Caroline L. Dusheck
Attorney, Agent, or Firm—Cushman Darby & Cushman

[57] ABSTRACT

Process for dyeing keratinous fibres, especially human keratinous fibres such as the hair, consisting in applying to these fibres a composition containing, in a medium suitable for dyeing, at least 2,6-dimethyl-1,4-diaminobenzene and/or 2,3-dimethyl-1,4-diaminobenzene and/or 2,6-diethyl-1,4-diaminobenzene, as well as its salts, and an oxidising agent, the pH of the composition applied to the fibres being less than 7 and the said composition not containing iodide ions in a sufficient quantity to oxidise the oxidation dye precursor.

21 Claims, No Drawings

PROCESS FOR DYEING KERATINOUS FIBRES WITH 2,6-DIMETHYL-1,4-DIAMINOBENZENE AND/OR 2,3-DIMETHYL-1,4-DIAMINOBENZENE AND/OR 2,6-DIETHYL-1,4-DIAMINOBENZENE IN AN ACID MEDIUM AND COMPOSITIONS EMPLOYED

This is a continuation of application Ser. No. 08/274,711, filed Jul. 18, 1994, now abandoned which is a continuation of application Ser. No. 07/996,193, filed Dec. 23, 1992, now abandoned which is a continuation of application Ser. No. 07/708,380, filed May 31, 1991, now abandoned.

The present invention relates to a new process for dyeing keratinous fibres, especially human keratinous fibres, employing 2,6-dimethyl-1,4-diaminobenzene and/or 2,3-dimethyl-1,4-diaminobenzene and/or 2,6-diethyl-1,4-diaminobenzene in combination with an oxidising agent in an acid medium, and to the compositions employed during this process.

It is known to dye keratinous fibres, and especially human hair, with dyeing compositions containing oxidation dye precursors, especially ortho- or para-phenylenediamines or ortho- or para-aminophenols, generally referred to as "oxidation bases".

It is also known that the hues obtained with these oxidation bases may be varied by combining them with couplers, referred to as colour modifiers, selected, in particular, from aromatic meta-diamines, meta-aminophenols and meta-diphenols.

The dyer of keratinous fibres generally seeks to obtain colorations having good resistance to light, washing, perspiration and adverse weather, in particular by the choice of oxidation bases enabling such results to be obtained.

Under the conditions used at the present time, the media of the oxidising composition and of the dyeing composition are alkaline. In point of fact, this alkalinity generally leads to a deterioration of the keratinous fibres.

To avoid or reduce this degradation of the keratinous fibres, it has been recommended more recently to apply to the fibres a mixture, prepared at the time of use, of the oxidising agent and certain oxidation dye precursors such as 1,4-diaminobenzene at an acid pH.

However, the Applicant found, in particular in the case of 1,4-diaminobenzene, that such a dyeing process led to profound changes in the kinetics of the reaction and in the dyeing of the fibres compared with the same dyeing process performed in an alkaline medium, and no longer satisfied the demands of the dyer.

The Applicant has just discovered that the use of 2,6-dimethyl-1,4-diaminobenzene and/or 2,3-dimethyl-1,4-diaminobenzene and/or 2,6-diethyl-1,4-diaminobenzene, in the presence of an oxidising agent in an acid medium, leads to colorations practically identical to those obtained under the usual conditions of use, and displays, moreover, surprisingly, greater resistance to the action of perspiration, shampoos, chemical treatments or environmental agents such as light.

The subject of the present invention is hence a process for dyeing keratinous fibres, especially human keratinous fibres such as the hair, comprising the application to these fibres of a composition containing at least one oxidation dye precursor, also known as an "oxidation base", selected from 2,6-dimethyl-1,4-diaminobenzene, 2,3-dimethyl-1,4-diaminobenzene or 2,6-diethyl-1,4-diaminobenzene, and at least one oxidising agent, at an acid pH.

The subject of the invention is also a dyeing agent containing two components, one of which components comprises the oxidation dye precursor and the other the oxidising agent at an acid pH, and in such quantities that the mixture has an acid pH.

The subject of the invention is also the ready-to-use composition containing the different agents used for dyeing the hair in an acid medium.

Other subjects of the invention will become apparent on reading the description of the examples which follow.

The process for dyeing keratinous fibres, and especially human keratinous fibres such as the hair, according to the invention, is essentially characterised in that at least one composition comprising, in a medium suitable for dyeing, an oxidation dye precursor selected from 2,6-dimethyl-1,4-diaminobenzene and/or 2,3-dimethyl-1,4-diaminobenzene or 2,6-diethyl-1,4-diaminobenzene, as well as the salts of these compounds and an oxidising agent, is applied to these fibres; the pH of the composition applied to the fibres is less than 7, and the said composition does not contain iodide ions in a sufficient quantity to oxidise the said oxidation dye precursor.

The oxidation dye precursors according to the present invention may be introduced into the dyeing composition either in the form of free bases or in the form of salts, for example in the form of hydrochlorides, hydrobromides, sulphates or tartrates.

The oxidising agent is preferably selected from hydrogen peroxide, urea peroxide, alkali metal bromates and persalts such as perborates and persulphates. Hydrogen peroxide is especially preferred.

The pH of the composition applied to the keratinous fibres, especially the hair, has a value of less than 7, and is preferably between 3 and 6.9. This pH is adjusted by the use of acidifying agents which are well known in the field of dyeing of keratinous fibres, and especially human hair, such as inorganic or organic acids, for example hydrochloric acid, phosphoric acid, carboxylic acids such as tartaric acid and citric acid, and sulphonic acids.

The compositions defined above, applied in the dyeing of keratinous fibres, can also contain, in addition, other oxidation dye precursors, either of the para type or of the ortho type, such as, for example: para-aminophenol, 2,5-diaminopyridine, 2-hydroxy-5-aminopyridine, 2,4,5,6-tetraaminopyrimidine, para-phenylenediamine, 2-chloro-para-phenylenediamine, ortho-aminophenols and ortho-phenylenediamines.

The dyeing compositions according to the present invention can also contain couplers which are known per se, such as meta-diphenols, meta-aminophenols, meta-phenylenediamines, meta-(N-acylamino)phenols, meta-ureidophenols, meta-carbalkoxyaminophenols, α-naphthol, ortho-diphenols and couplers possessing an active methylene group such as diketo compounds and pyrazolones.

Among these, there may be mentioned, in particular, 2,4-diamino-1,3-dimethoxybenzene, 2,4-dihydroxyphenoxyethanol, 2,4-dihydroxyanisole, meta-aminophenol, resorcinol, resorcinol monomethyl ether, 2-methyl-resorcinol, 2-methyl-5-[N-(β-hydroxyethyl)amino]phenol, 2-methyl-5-[N-(β-mesylaminoethyl)amino]phenol, 6-hydroxybenzomorpholine, 2,4-diaminoanisole, 2,4-diaminophenoxyethanol, 6-aminobenzomorpholine, 2-[N-(β-hydroxyethyl)amino]-4-aminophenoxyethanol, 2-amino4-[N-(β-hydroxyethyl)amino]anisole, 2,4-diaminophenyl β, γ-dihydroxypropyl ether, 2,4-diaminophenoxyethylamine, 2-methyl-5-aminophenol, 2,6-dimethyl-3-aminophenol, 3,4-methylenedioxyphenol, 3,4- methylenedioxyaniline and their salts. 2,6-Dimethoxy-1,3-diaminobenzene, meta-aminophenol, 2-methyl-5-[N-(β-hydroxyethyl)amino]phenol and α-naphthol are preferably used.

These compositions can also contain anionic, cationic, nonionic or amphoteric surfactants or mixtures thereof.

Among these surfactants, there may be mentioned alkylbenzenesulphonates, alkylnaphthalenesulphonates, fatty alcohol sulphates, ether sulphates and sulphonates, quaternary ammonium salts such as trimethylcetylammonium bromide and cetylpyridinium bromide, fatty acid ethanolamides, optionally oxyethylenated, polyoxyethylenated acids, alcohols or amines, polyglycerolated alcohols, polyoxyethylenated or polyglycerolated alkylphenols and also polyoxyethylenated alkyl sulphates.

The dyeing compositions are generally aqueous, but they can also Contain organic solvents to solubilise compounds which might not be sufficiently water-soluble.

Among these solvents, there may be mentioned, by way of example, $C_2$-$C_4$ lower alkanols such as ethanol and isopropanol, glycerol, glycols or glycol ethers such as 2-butoxyethanol, ethylene glycol, propylene glycol and diethylene glycol monoethyl ether and monomethyl ether, and also aromatic alcohols such as benzyl alcohol or phenoxyethanol, or mixtures of these solvents.

The compositions applied to the keratinous fibres according to the present invention can also contain thickening agents selected, in particular, from sodium alginate, gum arabic, cellulose derivatives such as methylcellulose, hydroxyethylcellulose, hydroxypropylcellulose, hydroxymethylcellulose and carboxymethylcellulose, acrylic acid polymers, optionally crosslinked, and xanthan gum. Inorganic thickening agents such as bentonite can also be used.

The composition can also contain antioxidants selected, in particular, from sodium sulphite, thioglycolic acid, sodium bisulphite, ascorbic acid and hydroquinone, as well as other cosmetically acceptable adjuvants when it is intended that the composition be used for dyeing human keratinous fibres, such as penetrating agents, sequestering agents, preservatives, buffers, fragrances, and the like.

The composition applied to the hair can take various forms, such as the form of liquids, creams or gels or any other form suitable for carrying out hair dyeing. It may be packaged in an aerosol can in the presence of a propellant.

The subject of the invention is also the ready-to-use composition used in the process defined above.

According to a preferred embodiment, the process comprises a preliminary step consisting in storing separately, on the one hand the composition containing, in a medium suitable for dyeing, 2,6-dimethyl-1,4-diaminobenzene and/or 2,3-dimethyl-1,4-diaminobenzene and/or 2,6-diethyl-1,4-diaminobenzene, in the form of a component (A), and on the other hand a composition containing the oxidising agent as defined above, in the form of a component (B), and in mixing them at the time of use before applying this mixture to the keratinous fibres, as described above. The component (A) does not contain iodide ions in a sufficient quantity to oxidise the said oxidation dye precursor.

The composition applied to the keratinous fibres results, in particular, from a mixture of 10 to 90% of the component (A) with 90 to 10% of the component (B) containing an oxidising agent.

The subject of the invention is also an agent for dyeing keratinous fibres, especially the hair, essentially characterised in that it contains at least two components, one consisting of the component (A) defined above and the other consisting of the component (B) also defined above, the pH of the components (A) and (B) being such that, after mixing in proportions of 90 to 10% for the component (A) and 10 to 90% for the component (B), the resulting composition has a pH of less than 7.

In this embodiment, the component (A), which contains at least the oxidation dye precursor, has a pH of between 3 and 10.5, and may be adjusted to the chosen value by means of alkalinising agents customarily used in the dyeing of keratinous fibres, such as ammonia solution, alkali metal carbonates, alkanolamines such as mono-, di- and triethanolamines and also their derivatives, or conventional acidifying agents such as inorganic or organic acids, for example hydrochloric and phosphoric acids, carboxylic acids such as tartaric and citric acids, and sulphonic acids.

This composition can contain the various other adjuvants mentioned above, in particular ortho or para oxidation dye precursors or couplers.

The oxidation dye precursors of the para or ortho type, other than 2,6-dimethyl-1,4-diaminobenzene, 2,3-dimethyl-1,4-diaminobenzene and 2,6-diethyl-1,4-diaminobenzene, are present in proportions of between 0.02 and 10% by weight, and preferably between 0.05 and 5% by weight, relative to the total weight of the component (A).

The couplers such as are mentioned above are present in concentrations of between 0.02 and 10% by weight, and preferably between 0.05 and 5% by weight, relative to the total weight of the component (A).

The concentration of 2,6-dimethyl-1,4-diamino-benzene and/or 2,3-dimethyl-1,4-diaminobenzene and/or 2,6-diethyl-1,4-diaminobenzene is between 0.02 and 10% by weight, and preferably between 0.05 and 5% by weight, relative to the total weight of the component (A).

The surfactants are present in the component (A) in proportions of 0.1 to 55% by weight.

The solvents optionally present in addition to water are present in proportions of between 0.5 and 40% by weight, and especially between 5 and 30% by weight, relative to the total weight of the component (A).

The thickening agents are preferably present in proportions of between 0.1 and 5%, and especially between 0.2 and 3%, by weight.

The antioxidants mentioned above are preferably present in the component (A) in proportions of between 0.02 and 1.5% by weight relative to the total weight of the component (A).

The component (A) according to the invention can take various forms, such as the form of liquids, creams or gels or any other form suitable for carrying out hair dyeing. It may be packaged in an aerosol can in the presence of a propellant.

The component (B) containing the oxidising agent as defined above has a pH of less than 7. This pH can have a minimum value of 1, and is preferably between 1.5 and 3.5. This component (B) may be acidified with the same type of acidifying agents as those used for the component (A).

It can take the form of liquids, more or less thickened, milks or gels.

The two-component dyeing agent according to the present invention may be packaged in a multi-compartment device or dyeing kit, or any other multi-compartment packaging system in which one of the compartments contains the component (A) and the second compartment contains the component (B); it being possible for these devices to be equipped with a means enabling the desired mixture to be delivered on the hair, such as the device described in the Applicant's Patent U.S. Pat. No. 4,823,985.

According to the invention, the dyeing process consists in applying the mixture obtained to the hair, in leaving it in place for 3 to 40 minutes and then in rinsing the hair and optionally shampooing.

The examples which follow are intended as illustrations of the invention, no limitation being implied.

EXAMPLES 1 to 10

Hair dyeing is performed by applying a mixture, prepared at the time of use, of the dyeing composition (A) and the oxidising composition (B) to permanent-waved grey hair which is 90% white. This mixture has the pH shown in the table of examples which follow.

This mixture is left to act for 30 minutes and the hair is then rinsed and shampooed.

After drying, the hair is dyed in the hue specified at the bottom of the table.

PROCEDURE

The composition described above is mixed, weight for weight, with "20 volumes" hydrogen peroxide and adjusted to pH 6.7 with orthophosphoric acid.

The preparation is applied to grey hair which is 90% white, on the basis of 28 g of the mixture per 3 g of hair, for 30 minutes. The locks are then rinsed, washed with a shampoo, rinsed and thereafter dried.

The hair is dyed in the hue specified at the bottom of the table:

| in g | 1 | 2 | 3 | 4 | 5 | 6 | 7 | 8 | 9 | 10 |
|---|---|---|---|---|---|---|---|---|---|---|
| A) Dyeing composition | | | | | | | | | | |
| 2,6-Dimethyl-1,4-di-amino-benzene.2 HCl | 0.627 | | | 0.657 | 0.657 | | | 0.438 | 0.876 | 0.583 |
| 2,3-Dimethyl-1,4-di-amino-benzene.2 HCl | | 0.627 | 0.627 | | | 0.627 | 0.627 | | | |
| 2-Methyl-5-[N-(β-hydroxyethyl)-amino]phenol | | 0.501 | | 0.417 | | 0.417 | | 0.324 | | 0.216 |
| meta-Aminophenol | | | | | | | | | 0.576 | 0.192 |
| α-Naphthol | 0.327 | | 0.327 | | 0.327 | | 0.327 | | | |
| Monoethanolamine qs pH | 9.8 | 9.8 | 9.8 | 8.8 | 8.8 | 8.9 | 8.8 | 9.1 | 8.8 | 8.9 |
| Vehicle 1 | X | X | X | | | | | | | |
| Vehicle 2 | | | | X | X | X | X | X | X | X |
| Water qs | 100 | 100 | 100 | 100 | 100 | 100 | 100 | 100 | 100 | 100 |
| B) Oxidising composition | | | | | | | | | | |
| Hydrogen peroxide solution, "20 volumes" Phosphoric acid qs pH | 1.5 | 1.5 | 1.5 | 1.5 | 1.5 | 1.5 | 1.5 | 1.1 | 1.5 | 1.1 |
| pH w/w mixture A + B | 5.5 | 5.5 | 5.5 | 6.0 | 6.4 | 6.0 | 6.1 | 6.6 | | 6.5 |
| pH mixture ⅓ A + ⅔ B | | | | | | | | | 5.8 | |
| Hues obtained: | light blond | iridescent blond | matt ashen light blond | deep greyish purple | greyish olive | deep purple iridescent | greyish yellowish blond | deep purple irridescent | blueish deep grey | slightly ashen dark auburn |

EXAMPLES 11 and 12

| COMPOSITION | |
|---|---|
| Dye | X g |
| Nonylphenol containing 4 moles of ethylene oxide, sold by the company HENKEL under the name "SINNOPAL NP4" | 25.5 g |
| Nonylphenol containing 9 moles of ethylene oxide, sold by the company HENKEL under the name "SINNOPAL NP9" | 17.5 g |
| Ethylene glycol butyl ether | 7.0 g |
| Propylene glycol | 11.0 g |
| Ethyl alcohol | 2.0 g |
| Monoethanolamine lauryl ether sulphate sold by the company LEVER at a concentration of 28% AS under the name "SACTIPON 2 OM 29" | 17.9 g |
| Sodium acetate | 0.8 g |
| Antioxidant, sequestering agent qs | |
| Demineralised water qs | 100.0 g |

| in g | Example 11 | Example 12 |
|---|---|---|
| 2,6-Diethyl-1,4-diaminobenzene | 0.711 | 0.711 |
| 6-Hydroxybenzomorpholine | 0.453 | |
| 2,4-Diaminophenoxyethanol.2 HCl | | 0.723 |
| Hues obtained: | matt yellow | blueish medium grey |

EXAMPLES 13 and 14

Hair dyeing is performed by applying a mixture, prepared at the time of use, of the dyeing composition (A) and the oxidising composition (B) to permanent-waved grey hair which is 90% white.

This mixture has the pH shown in the table of examples which follow.

This mixture is left to act for 30 minutes and the hair is then rinsed and shampooed. After drying, the hair is dyed in the hue specified at the bottom of the table below:

| in g | 13 | 14 |
|---|---|---|
| A) Dyeing composition | | |
| 2,6-Dimethyl-1,4-diaminobenzene.2 HCl | 0.836 | 0.836 |
| 2-Methylresorcinol | | 0.248 |
| 2-Methyl-5-[N-(β-hydroxyethyl)amino]phenol | 0.19 | |
| 2-Chloro-para-phenylenediamine sulphate | | 0.48 |
| 6-Hydroxybenzomorpholine | 0.464 | |
| Monoethanolamine qs pH | 9.9 | 9.8 |
| Vehicle 3 | X | X |
| Water qs | 100 | 100 |
| B) Oxidising composition | | |
| Hydrogen peroxide solution, "20 volumes" | | |
| Orthophosphoric acid qs pH | 1.2 | 1.2 |
| pH w/w mixture of A + B | 6.6 | 6.3 |
| Hues obtained: | slightly matt golden light chestnut | irridescent golden deep blond |

DYEING VEHICLE 1

| | |
|---|---|
| Nonylphenol containing 4 moles of ethylene oxide, sold by the company HENKEL under the name "SINNOPAL NP4" | 25.5 g |
| Nonylphenol containing 9 moles of ethylene oxide, sold by the company HENKEL under the name "SINNOPAL NP9" | 17.5 g |
| Ethylene glycol butyl ether | 7.0 g |
| Propylene glycol | 11.0 g |
| Ethyl alcohol | 2.0 g |
| Monoethanolamine lauryl ether sulphate sold by the company LEVER at a concentration of 28% AS under the name "SACTIPON 2 OM 29" | 5.0 g AS |
| Sodium metabisulphite in aqueous solution containing 35% AS | 0.45 g AS |
| Sodium acetate | 0.8 g |
| Antioxidant, sequestering agent qs | |

DYEING VEHICLE 2

| | |
|---|---|
| Polyglycerolated oleyl alcohol containing 2 moles of glycerol | 4.0 g |
| Polyglycerolated oleyl alcohol containing 4 moles of glycerol at a concentration of 78% AS | 5.69 g AS |
| Oleic acid | 3.0 g |
| Oleylamine containing 2 moles of ethylene oxide, sold by the company AKZO under the name "ETHOMEEN O 12" | 7.0 g |
| Diethylaminopropyl laurylaminosuccinamate sodium salt containing 55% AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% AS | 0.45 g AS |
| Ammonium acetate | 0.8 g |
| Antioxidant, sequestering agent qs | |

DYEING VEHICLE 3

| | |
|---|---|
| Cetyl/stearyl alcohol | 18.0 g |
| 2-Octyldodecanol | 3.0 g |
| Oxyethylenated cetyl/stearyl alcohol containing 15 moles of ethylene oxide | 3.0 g |
| Ammonium lauryl sulphate containing 30% AS | 3.6 g AS |
| Ammonium thiolactate containing 50% AS | 0.4 g AS |

I claim:

1. A process for dyeing keratinous fibers comprising applying to said fibers in an amount effective to dye said fibers an acid composition comprising in an aqueous medium suitable for dyeing said fibers a mixture of (i) an oxidation dye precursor selected from the group consisting of 2,6-dimethyl-1,4diaminobenzene, 2,3-dimethyl-1,4-diaminobenzene, 2,6-diethyl-1,4diaminobenzene and mixtures thereof, said oxidation dye precursor being present in an amount ranging from 0.02 to 10 percent by weight based on the total weight of said composition, (ii) an oxidizing agent present in an amount effective to oxidize said oxidation dye precursor, and (iii) an acid component present in a sufficient amount such that the said mixture has a pH less than 7, the said acid composition not containing iodide ions in an amount sufficient to oxidize said oxidation dye precursor.

2. The process of claim 1 wherein said oxidizing agent is selected from the group consisting of hydrogen peroxide, urea peroxide, an alkali metal bromate and a persalt.

3. The process of claim 1 wherein the pH of said mixture ranges from 3 to 6.9.

4. The process of claim 1 wherein said composition also contains one or both of an oxidation dye precursor selected from a para oxidation dye precursor and an ortho oxidation dye precursor, and present in an amount ranging from 0.02 to 10 percent by weight.

5. The process of claim 1 wherein said composition also contains from 0.02 to 10 percent by weight of a coupler selected from the group consisting of a meta-diphenol, a meta-aminophenol, a meta-ureidophenol, a meta-phenylenediamine, a meta-acylaminophenol, a meta-carbalkoxyaminophenol, α-naphthol, an ortho-diphenol, a diketo compound and a pyrazolone.

6. The process of claim 5 wherein said coupler is selected from the group consisting of 2,4-diamino-1,3dimethoxybenzene, 2,4-dihydroxyphenoxyethanol, 2,4dihydroxyanisole, meta-aminophenol, resorcinol, resorcinol monomethyl ether, 2-methylresorcinol, 2-methyl-5-[N-(β-hydroxyethyl)amino]phenol, 2-methyl-5-[N-(β-mesylaminoethyl)amino]phenol, 6-hydroxybenzomorpholine, 2,4-diaminoanisole, 2,4diaminophenoxyethanol, 6-aminobenzomorpholine, 2-[N-(β-hydroxyethyl)amino]-4-aminophenoxyethanol, 2-amino-4-[N-(β-hydroxyethyl)amino]-anisole, 2,4-diaminophenyl β,γ-dihydroxypropyl ether, 2,4-diaminophenoxyethylamine, 2-methyl-5aminophenol, 2,6-dimethyl-3-aminophenol, 3,4-methylenedioxyphenol, 3,4-methylenedioxyaniline and their salts.

7. The process of claim 1 wherein said composition also contains at least one of an anionic, cationic, nonionic or amphoteric surfactant present in an amount ranging from 0.1 to 55 weight percent, an antioxidant present in an amount ranging from 0.02 to 1.5 weight percent and a thickening agent present in an amount ranging from 0.1 to 5 weight percent.

8. The process of claim 1 wherein said aqueous medium suitable for dyeing said fibers is water or a mixture of water and a solvent selected from the group consisting of a $C_2$–$C_4$ lower alkanol, glycerol, glycol, glycolether, diethyleneglycol, monoethylether, diethyleneglycol monomethyl ether, an aromatic alcohol and mixtures thereof.

9. The process of claim 1 wherein said composition is permitted to remain in contact with said fibers for a period of time ranging from 3 to 40 minutes, after which said fibers are rinsed and dried.

10. The process of claim 9 which includes, subsequent to rinsing said fibers and prior to drying said fibers, Shampooing and rinsing said fibers.

11. The process of claim 1 where in said composition said acid component is selected from the group consisting of hydrochloric acid, phosphoric acid, tartaric acid, citric acid and sulphonic acid.

12. A composition for dyeing keratinous fibers comprising a component A containing in an aqueous medium suitable for dyeing said fibers at least one oxidation dye precursor selected the group consisting of 2,6-dimethyl-1,4-diaminobenzene, 2,3-dimethyl-1,4-diaminobenzene, 2,6-diethyl-1,4-diaminobenzene and mixtures thereof, said oxidation dye precursor being present in an amount ranging from 0.02 to 10 percent by weight based on the total weight of said component A, said component A not containing iodide ions in an amount sufficient to oxidize said oxidation dye precursor, and a component B comprising in an aqueous medium suitable for dyeing said fibers, an oxidizing agent present in an amount effective to oxidize said oxidation dye precursor, and an acid component in a sufficient amount such that a mixture in proportions of 90 to 10% of said component A and of 10 to 90% of said component B, the said composition has a pH less than 7.

13. The composition of claim 12 wherein said component A has a pH ranging from 3 to 10.5.

14. The composition of claim 12 wherein said component A also contains one or both of (a) an oxidation dye precursor selected from a para oxidation dye precursor and an ortho oxidation dye precursor or a mixture thereof present in an amount ranging from 0.02 to 10 percent by weight and (b) a coupler present in an amount ranging from 0.02 to 10 percent by weight.

15. The composition of claim 12 wherein said oxidation dye precursor is present in an amount ranging from 0.02 to 10 percent by weight relative to the total weight of said composition.

16. The composition of claim 12 which also contains at least one of a surfactant present in an amount ranging from 0.1 to 35 weight percent, a solvent, in addition to water, present in an amount ranging from 0.5 to 40 weight percent, a thickening agent present in an amount ranging from 0.1 to 5 weight percent, and an antioxidant present in an amount ranging from 0.02 to 1.5 weight percent.

17. The composition of claim 12 wherein said component B has a pH ranging from 1 to less than 7.

18. The composition of claim 12 where in said component B, said acid component is selected from the group consisting of hydrochloric acid, phosphoric acid, tartaric acid, citric acid 6and sulphonic acid.

19. A multicompartment kit for dyeing keratinous fibers comprising a first compartment housing component A defined in claim 12 and a second compartment housing component B defined in claim 12.

20. A process for dyeing keratinous fibers comprising admixing 90 to 10 weight percent of a component A containing in an aqueous medium suitable for dyeing said fibers at least one oxidation dye precursor selected from the group consisting of 2,6-dimethyl-1,4-diaminobenzene, 2,3-dimethyl-1,4-diaminobenzene, 2,6-diethyl-1,4-diaminobenzene and mixtures thereof, present in an amount ranging from 0.02 to 10 percent by weight based on the total weight of said component A, said component A not containing iodide ions in an amount effective to oxidize said oxidation dye precursor, with 10 to 90 weight percent of a component B containing, in an aqueous medium suitable for dyeing said fibers, at least one oxidizing agent in a sufficient amount to oxidize said oxidation dye precursor and an acid component in a sufficient amount such that the resulting mixture has a pH less than 7 and immediately applying said mixture to said fibers in an amount effective to dye said fibers.

21. The process of claim 19 where in said component B, said acid component is selected from the group consisting of hydrochloric acid, phosphoric acid, tartaric acid, citric acid and sulphonic acid.

* * * * *